United States Patent [19]
Durham et al.

[11] 4,205,076
[45] May 27, 1980

[54] LIPOGENESIS INHIBITION BY CERTAIN ESTERS OF SUBSTITUTED BENZODIOXINCARBOXYLIC ACIDS

[75] Inventors: Harry G. Durham, Modesto, Calif.; John B. Carr, Houston, Tex.

[73] Assignee: Shell Oil Company, Houston, Tex.

[21] Appl. No.: 33,635

[22] Filed: Apr. 26, 1979

Related U.S. Application Data

[63] Continuation-in-part of Ser. No. 951,535, Oct. 16, 1978, abandoned.

[51] Int. Cl.$^2$ ............................................. A61K 31/425
[52] U.S. Cl. .................................. 424/270; 260/340.3; 424/278; 548/204

[58] Field of Search ........................ 260/340.3, 302 H; 424/278, 270

[56] References Cited

U.S. PATENT DOCUMENTS

| | | |
|---|---|---|
| 3,777,017 | 12/1973 | McGovern et al. .......... 260/340.3 X |
| 4,103,021 | 7/1978 | Carr .................................... 424/278 |
| 4,118,507 | 10/1978 | Carr .................................... 424/278 |

*Primary Examiner*—Ethel G. Love

[57] ABSTRACT

Use as lipogenesis inhibitors in mammals of alkyl esters of certain substituted 2,3-dihydro-1,4-benzodioxincarboxylic acids.

1 Claim, No Drawings

LIPOGENESIS INHIBITION BY CERTAIN ESTERS OF SUBSTITUTED BENZODIOXINCARBOXYLIC ACIDS

This application is a continuation-in-part of application Ser. No. 951,535, filed on Oct. 16, 1978, now abandoned.

DESCRIPTION OF THE INVENTION

It has been found that lipogenesis in mammals is inhibited by alkyl esters of certain substituted 2,3-dihydro-benzodioxin-2-carboxylic acids, of the formula

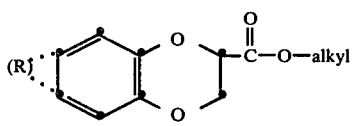

wherein "alkyl" is straight-chain or branched-chain alkyl of from one to four carbon atoms, and R is a moiety which is one of: formyl, acetyl, (hydroxyimino)methyl, 1-(hydroxyimino)ethyl, (methoxyimino)methyl, 1-(methoxyimino)ethyl, benzoyl, acetamido, amino, benzamido, methylsulfonylamino, and 2-methyl-4-thiazolyl.

In Formula I, the dotted lines from the moiety R to the carbon atoms in the ring are intended to indicate that the moiety can be bonded to the carbon atom at the 6-position, or a carbon atom at the 7-position, of the ring structure.

Methods by which the compounds of this invention can be prepared ordinarily produce mixtures of the 6-substituted and 7-substituted species. Such mixtures, as well as deliberate mixtures, of the 6- and 7-substituted species, as well as each of the individual 6- and 7-substituted species, are contemplated in this invention.

Chirality exists in the compounds of Formula I due to the asymmetric structural configuration at the 2-position of the 2,3-dihydro-1,4-benzodioxin ring. As a result, each of these compounds exists in the forms of two optical isomers. The individual isomers have not been separated, so that their respective activity as lipogenesis inhibitors has not been determined. The invention contemplates each of the individual active isomers, as well as racemic, and other mixtures thereof.

Typical, exemplary, individual species of the compounds of Formula I, and their preparation, are described in actual examples set out hereinafter. Other typical, exemplary, individual species are those below wherein, referring to Formula (I), "alkyl" and the moiety R, and its position on the ring structure, are as follows:

| "alkyl" | R |
|---|---|
| ethyl | 7-formyl |
| ethyl | 7-(hydroxyimino)methyl |
| methyl | 7-(methoxyimino)methyl |
| ethyl | 7-(1-methoxyimino)ethyl) |
| ethyl | 7-benzoyl |
| ethyl | 7-acetamido |
| methyl | 7-acetyl |
| n-propyl | 7-acetyl |
| isopropyl | 7-acetyl |
| 1-methylpropyl | 7-acetyl |
| ethyl | 7-amino |
| ethyl | 7-benzamido |

| "alkyl" | R |
|---|---|
| ethyl | 7-methylsulfonylamino | and the 6-position counterparts of these species.

The compounds of Formula I can be prepared by the following procedures.

In each of these examples, the identities of the products, and the intermediates involved, were confirmed by appropriate elemental and spectral analyses.

EXAMPLE 1 Ethyl 7(and 6)-acetyl-2,3-dihydro-1,4-benzodioxin-2-carboxylate (1)

400 ml of a mixture of 1:8 v/v glacial acetic acid in water was added in two portions to a stirred mixture of 35 g of 4-(chloroacetyl)-catechol in 300 ml of ethanol. At 10 minute intervals, four 10 g portions of 90% zinc dust were added, the mixture being held below about 45° C. The mixture then was stirred for 2 hours at 30°–40° C. and allowed to stand over a weekend. The liquid phase was decanted and stripped to a quarter of its volume under reduced pressure. The residue was extracted with ether. The ether extract was washed with sodium bicarbonate solution. The solvent was evaporated. The solid residue was recrystallized from toluene to give 4-acetylcatechol (1A), mp: 118°–119° C.

150 g of ethyl 2,3-dibromopropionate was added over a 3-hour period to a stirred slurry of 96 g of 1A 234 g of potassium carbonate and 600 ml of acetone. The temperature of the mixture rose from 23° C. to 40° C. The mixture then was refluxed (55° C.) for 19 hours, and filtered. The acetone was evaporated from the filtrate under reduced pressure. The residue was distilled to give 1, as a colorless liquid, bp: 165°–166° C., 0.1 Torr.

EXAMPLE 2 Ethyl 2,3-dihydro-7(and 6)-(1-(hydroxyimino)ethyl)-1,4-benzodioxin-2-carboxylate (2)

A mixture of 18 g of 1, 75 ml of methanol, 5.2 g of hydroxylamine hydrochloride, 50 ml of water and 4.0 g of sodium carbonate was heated on a steam bath for 35 minutes and allowed to stand overnight. The solid which formed was separated and recrystallized from benzene to give 2, mp: 111°–113° C.

EXAMPLE 3 Ethyl 2,3-dihydro-7-(1-(methoxyimino)ethyl)-1,4-benzodioxin-2-carboxylate (3)

22.8 g of 1 was dissolved in 100 ml of ethanol. A solution of 7.94 g of methoxylamine hydrochloride and 5.5 g of sodium carbonate in 75 ml of water was added. The mixture was heated and stirred at reflux temperature for 4 hours, then was allowed to cool and held at room temperature over a weekend. The mixture was diluted with 50 ml of water and the solvents were evaporated. The residue was extracted with ether. The extract was dried (MgSO₄) and filtered. The solvent was evaporated from the filtrate and the residue was chromatographed over silica gel, using a 1:1 v/v mixture of ether and hexane as eluent. The major absorption band was worked up to give an oil, which was distilled in a Kugelrohr apparatus to give (3), b.p.: 136°–138° C. (0.12 Torr.).

EXAMPLE 4 Ethyl 6(and 7)-(acetylamino)-2,3-dihydro-1,4-benzodioxin-2-carboxylate (4)

68 g of phosphorus pentachloride was added in portions over a 15-minute period to a stirred solution of 50 g of 2 in 1000 ml of chloroform. The mixture was refluxed for 2 hours, allowed to cool while being stirred, then, with stirring, was poured into 1000 ml of ice water. The organic phase was separated, washed with water, then with 10% sodium bicarbonate solution, dried (MgSO$_4$) and filtered. The solvent was evaporated from the filtrate under reduced pressure. The residue was triturated with 60 ml of ethanol. The mixture was stored in a freezer overnight. The solid which formed was collected and washed with ethanol, then ether, and dried under reduced pressure. The product was dissolved in 100 ml of hot ethanol; the solution was filtered through charcoal and chilled in a freezer over a weekend, and filtered. The solid was refluxed in 200 ml of ether for ½ hour and the resulting mixture was filtered. The solid was chromatographed over silica gel using chloroform as eluent. The appropriate fractions were extracted with chloroform and the solvent was evaporated from the extract under reduced pressure. The residue was again chromatographed over silica gel, using chloroform as eluent. The appropriate fractions were extracted with chloroform and the solvent was evaporated from the extract under reduced pressure. The residue was dissolved in 90 ml of hot ethanol, the solution was filtered through charcoal and chilled in a freezer overnight. The solid was collected, dissolved in hot ethanol; the solution was filtered through charcoal and chilled in a freezer. The solid was collected, ground and dried to give 4, as a solid, mp: 146°–147° C.

EXAMPLE 5 Ethyl 7-benzoyl-2,3-dihydro-1,4-benzodioxin-2-carboxylate (5)

A solution of 110.1 g of catechol and 202 g of triethylamine in 1000 ml of tetrahydrofuran was added drop-by-drop to a stirred solution of 295.2 g of benzoyl chloride in 1000 ml of tetrahydrofuran, at about 10° C. The stirred mixture then was allowed to warm to room temperature and stirred for 2 hours. The mixture was filtered and the solvent was evaporated from the filtrate under reduced pressure (40° C.). The residue was suspended in 500 ml of ligroin and stored overnight, then filtered. The solid was washed with petroleum ether and dried at room temperature under reduced pressure, to give catechol dibenzoate (5A), as a yellow crystalline solid.

56 g of aluminum chloride was added to a stirred solution of 65 g of 5A in 180 ml of nitrobenzene and the suspension was refluxed for 5 hours, then stored overnight. Then 800 ml of ice water was added, followed by 25 ml of concentrated hydrochloric acid. The nitrobenzene was removed by steam distillation. The aqueous phase was decanted and 333 ml of 3 N sodium hydroxide solution was added to the residue. The mixture was refluxed for 3 hours. Concentrated hydrochloric acid was added to the stirred, cooled mixture until the pH of the mixture was about 1. The mixture again was refluxed, filtered through charcoal and the filtrate was placed in a refrigerator. The solid was collected, dried under reduced pressure (80° C.), and recrystallized from 350 ml of hot water to give 3,4-dihydroxybenzophenone (5B).

11.63 ml of ethyl 2,3-dibromopropionate was added drop-by-drop over a 15-minute period to a mixture of 15.9 g of 5B, 58.5 g of anhydrous potassium carbonate and 250 ml of acetone. The stirred mixture was refluxed for 7 hours and stored overnight. The mixture was filtered and the solvent was evaporated from the filtrate under reduced pressure (40° C.). The residue was suspended in 600 ml of ether and the mixture was washed with water, then with sodium bicarbonate solution, then dried (MgSO$_4$). The solvent was evaporated under reduced pressure. The residue was chromatographed over silica gel using chloroform as eluent. Workup with ether and removal of the solvent gave a residue which was suspended in ethanol and placed in a freezer overnight. The solid was collected, washed with ethanol and dried to give 5, mp: 70°–71° C.

EXAMPLE 6 Ethyl 6(and 7)-(2'-methyl-4'-thiazolyl)-2,3-dihydro-1,4-benzodioxin-2-carboxylate (6)

A solution of 56.0 g of alpha-chloro-3',4'-dihydroxyacetophenone in 400 ml of 1,2-dimethoxyethane was added drop-by-drop to a solution of 23.0 g of thioacetamide in 300 ml of 1,2-dimethoxyethane. The mixture was heated and refluxed for 20 hours. The precipitate which formed was collected and dried. It was suspended in water and dilute (10%) sodium hydroxide solution was added until the pH of the mixture was about 6. The precipitate was collected and dried to give 4-(2'-methyl-4'-thiazolyl)catechol, (6A).

40.9 g of ethyl 2,3-dibromopropionate was added drop-by-drop to a mixture of 31.1 g of 6A, 53.9 g of anhydrous potassium carbonate, and 750 ml of acetone, at reflux. The resulting mixture was heated at reflux for 18 hours, then was filtered. The filtrate was concentrated, the residue dissolved in 500 ml of ether and the resulting mixture was filtered. The filtrate was washed sequentially with water, 5% solution hydroxide solution, and water. The ether phase was separated, dried (MgSO$_4$) and concentrated. The resulting oil was chromatographed on silica gel, using a 1:1 v/v mixture of hexane and ether as eluent. The fraction containing the product was extracted with ether, and the ether was evaporated under reduced pressure to give an oil. The oil was distilled to give 6, bp: 168°–172° C. (0.15 Torr.).

The individual species wherein R is formyl can be prepared from 3,4-dihydroxybenzaldehyde according to the procedures described in Example 1.

The species wherein R is amino can be prepared by hydrolysis of the species wherein R is acetamido. The species wherein R is methylsulfonylamino can be prepared by treating the species wherein R is amino with methanesulfonyl chloride. The species wherein R is benzamido can be prepared by treating the species wherein R is amino with benzoyl chloride.

Esters of Formula I have been found to inhibit lipogenesis in tissues of mammals. The manner in which they cause this effect is not known with certainty; it is believed that they interfere with the synthesis of fatty acids in the tissues. Their effectiveness for this purpose has been ascertained by immersing samples of swine adipose tissue in a liquid medium containing radioactive glucose and the test chemical for a period of time, then isolating the lipid from the treated tissue and determining the incorporation of the radioactive carbon into lipid by means of scintillation counting techniques. These tests were conducted in swine adipose tissues because in swine, the primary site of lipogenesis—i.e., fatty acid synthesis—appears to be adipose tissue.

Described in more detail, tests were conducted according to the following general procedure:

150 milligrams of slices of swine adipose tissue were incubated at 37° C. for 2 hours with shaking in 3 milliliters of Krebs-Ringer bicarbonate solution containing one-half the normal calcium ion concentration, 60 micromoles of glucose, 0.5 micro-Curie of glucose-U$^{14}$C, and 300 microunits of insulin, and 5% dimethyl sulfoxide (DMSO). The test compounds were added as a solution or suspension in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform/methanol (2:1 v/v). The extracts were washed according to Folch et al. (J. Biol. Chem. 226, 497–509, (1957)), air dried, and counted in a liquid scintillation counter with 15 milliliters of counting fluid (two parts toluene containing 0.4% w/v New England Nuclear Omnifluor/1 part Triton X-100). The tests were conducted in triplicate and were accompanied by control tests in which all ingredients, proportions and conditions were the same except that no test compound was included. From the data obtained were calculated the percent inhibition of lipid synthesis by the test compounds in each case. The data obtained from the tests are set out in Table 1, as the percent inhibition of lipogenesis compared to the results obtained in the control tests wherein only the test compound was omitted.

Table I

| Compound No. | Percent Inhibition |
| --- | --- |
| 1 | 89 |
| 2 | 94 |
| 3 | 52 |
| 4 | 96 |
| 5 | 69 |
| 6 | 79 |

The esters of Formula I can be used to control lipogenesis in mammals such as, for example, pets, animals in a zoo, livestock, furbearing animals and domestic animals, including, but not limited to dogs, cats, mink, sheep, goats, swine, cattle, horses, mules and donkeys. The effect is obtained by administering an effective amount of one or a mixture of two or more of the esters orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parental administration, they may be in the form of a solution, suspension, dispersion or emulsion. They can be administered in the form of an implant or other controlled sustained release formulation. Inert carriers, such as one or more of water, edible oil, gelatin, lactose, starch, magnesium sterate, talc or vegetable gum can be used. The dosage of the ester needed to inhibit lipogenesis will depend upon the particular ester used, and the particular animal being treated. However, in general, satisfactory results are obtained when the esters are administered in a dosage of from about 1 to about 400 milligrams per kilogram of the animal's body weight. The ester can be administered in a single dose or in a series of doses in the same day, or over a period of days. For any particular animal, a specific dosage regimen should be adjusted according to the individual need, the particular ester(s) used as the inhibitor, and the professional judgment of the person administering or supervising the administration of the inhibitor. It is to be understood that the dosages set forth herein are exemplary only, and that they do not, to any extent, limit the scope or practice of the invention.

I claim as my invention:

1. A method of inhibiting lipogenesis in a mammal, which comprises administering, to a mammal in need of such treatment, orally or parenterally a lipogenesis inhibiting amount of a compound of the formula

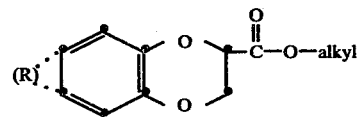

wherein "alkyl" is alkyl of from one to four carbon atoms, and R is a moiety which is one of: formyl, acetyl, benzoyl, acetamido, (hydroxyimino)methyl, 1-(hydroxyimino)ethyl, (methoxyimino)methyl, 1-(methoxyimino)ethyl, amino, benzamido, methylsulfonylamino, and 2-methyl-4-thiazolyl.

* * * * *